United States Patent
Kalinichev et al.

(10) Patent No.: US 9,752,999 B2
(45) Date of Patent: Sep. 5, 2017

(54) MOISTURE INGRESS SENSORS

(71) Applicant: Apple Inc., Cupertino, CA (US)

(72) Inventors: Kirill Kalinichev, San Francisco, CA (US); Kevin M. Keeler, Los Gatos, CA (US); Brian C. Menzel, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/290,866

(22) Filed: May 29, 2014

(65) Prior Publication Data
US 2015/0346127 A1    Dec. 3, 2015

(51) Int. Cl.
*G01R 27/08* (2006.01)
*G01R 27/26* (2006.01)
*G01R 31/08* (2006.01)
*G01R 31/3187* (2006.01)
*G01N 5/02* (2006.01)
(Continued)

(52) U.S. Cl.
CPC ......... *G01N 27/048* (2013.01); *G01N 27/121* (2013.01); *H02H 5/083* (2013.01)

(58) Field of Classification Search
CPC .... G01R 27/08; G01R 31/08; G01R 31/3187; G01N 27/048; G01N 5/02
USPC ....... 324/640, 663, 665, 678, 689, 690, 694; 73/73
See application file for complete search history.

(56) References Cited

U.S. PATENT DOCUMENTS

| | | | |
|---|---|---|---|
| 5,606,264 A * | 2/1997 | Licari | G01N 27/048 324/696 |
| 7,571,637 B2 * | 8/2009 | Chen | G01N 27/223 73/73 |

(Continued)

FOREIGN PATENT DOCUMENTS

CN    1343308 A    4/2002
CN    2745259 Y    12/2005
(Continued)

OTHER PUBLICATIONS

Chinese Patent for Utility Model No. ZL201520353897.6—Utility Model Patentability Evaluation Report (UMPER) dated Jan. 26, 2016.
Chinese Application for Invention No. 201510282024.5—First Office Action dated May 27, 2017.

*Primary Examiner* — Tung X Nguyen
*Assistant Examiner* — Neel Shah
(74) *Attorney, Agent, or Firm* — Downey Brand LLP (57) ABSTRACT

This application relates to a moisture ingress sensor. In particular, this application relates to a moisture ingress sensor that can detect liquid ingress into an electronic device. The moisture ingress sensor can include a resistor, an N-channel MOSFET, an operation amplifier, comparators, and an AND logic gate. The moisture ingress sensor is configured to provide a lower power means for accurately detecting moisture in an electronic device. Multiple areas of the electronic device can include the moisture ingress sensor in order to optimize the detection of moisture for at a variety of regions of the electronic device. Additionally, the electronic device can record signals from the moisture ingress sensor and shut down components of the electronic device that could be affected by the detected moisture. Furthermore, the moisture ingress sensor can be tuned to detect one or more types of liquids.

20 Claims, 11 Drawing Sheets

(51) Int. Cl.
    *G01N 27/04*     (2006.01)
    *H02H 5/08*     (2006.01)
    *G01N 27/12*     (2006.01)

(56) References Cited

U.S. PATENT DOCUMENTS

| | | |
|---|---|---|
| 7,973,667 B2 | 7/2011 | Crnkovich et al. |
| 8,236,164 B2 | 8/2012 | Gustafsson et al. |
| 8,773,271 B1 * | 7/2014 | Stevens .................. H03K 17/94 340/604 |
| 2002/0136664 A1 | 9/2002 | Lee et al. |
| 2011/0109333 A1 * | 5/2011 | Porjo ...................... G01M 3/16 324/694 |
| 2011/0295504 A1 | 12/2011 | Barber et al. |
| 2012/0038374 A1 * | 2/2012 | Johnson ................ G01M 3/045 324/694 |
| 2015/0070179 A1 | 3/2015 | Wu et al. |
| 2015/0372479 A1 | 12/2015 | Xia |

FOREIGN PATENT DOCUMENTS

| | | |
|---|---|---|
| CN | 101505812 A | 8/2009 |
| CN | 202309804 U | 7/2012 |
| CN | 102904211 A | 1/2013 |
| CN | 102984319 A | 3/2013 |
| CN | 103227871 A | 7/2013 |
| EP | 0 635 123 B1 | 3/1997 |
| WO | 03/046500 A1 | 6/2003 |
| WO | WO2013155764 A1 | 10/2013 |

\* cited by examiner

MOISTURE INGRESS SENSORS

FIELD

The described embodiments relate generally to moisture sensors. More particularly, the present embodiments relate to moisture ingress sensors for detecting the ingress of liquid in an electronic device.

BACKGROUND

Moisture ingress is a common problem for electronic devices because of the ability of liquids to cause shorts and corrosion within an electronic device. Often times, an electronic device may contact a liquid but only manifest symptoms of moisture ingress after an extended period of time. In the case of a mobile phone, where certain features of a mobile phone may only be used occasionally, a substantial amount of time may pass before a user notices the degeneration of certain features of the mobile phone caused by moisture ingress. For example, a headphone jack of a mobile phone may be rarely utilized by users who do not play music through their phone or conduct phone calls through a wearable headset. However, should the headphone jack contact a liquid, the headphone jack could be shorted by the liquid and degrade other portions of the mobile phone as the liquid progresses through the mobile phone. If a user is not aware of the liquid ingress, they may not be able to shut off the mobile phone in time to prevent shorting. Moreover, even if the user was made aware of the liquid ingress, they may not be provided with any way of mitigating damage caused by shorting and corrosion within the mobile device.

SUMMARY

This paper describes various embodiments that relate to moisture ingress sensors. In some embodiments, an apparatus is set forth as having a moisture interface element and a logic circuit connected to the moisture interface element. The apparatus can further include an amplifier circuit connected to the logic circuit and the moisture interface element. Additionally, when the moisture interface element contacts moisture, the apparatus can transmit an activating signal through the amplifier circuit and the logic circuit can output a moisture indication signal. If the apparatus is configured within a computing device, the moisture indication can be received by a processor in the computing device and respond according to a protocol stored within the computing device.

In some embodiments, a moisture ingress sensor is set forth herein as having a moisture interface element and a bias switch connected to the moisture interface element. The moisture ingress sensor can further include an operational amplifier and N-channel (metal oxide semiconductor field effect transistor) MOSFET connected between the moisture interface element and a grounded bias resistor. Additionally, the moisture ingress sensor can include a logical component and a comparator coupled to the N-channel MOSFET and the moisture interface element. The moisture ingress sensor can be configured to provide a moisture indication signal as a result of the moisture interface element contacting a liquid and an activation signal being transmitted through the N-channel MOSFET. Moreover, the moisture indication signal can be sent when a reference voltage received at the comparator is within a predetermined tolerance defined by the comparator. Thereafter, the moisture indication signal can be used by a computing device in which the moisture ingress sensor can be installed to shut down portions of the computing device to mitigate damage caused by the liquid.

Furthermore, in some embodiments, a system and a machine-readable non-transitory storage medium are set forth to carry out steps that include providing a periodic voltage signal to the moisture ingress sensor. The steps can also include causing a logic component of the moisture ingress sensor to send a moisture indication when the moisture ingress sensor contacts a liquid. Additionally, the steps can include receiving a moisture indication from the moisture ingress sensor and sending a switch signal to open a bias switch of the moisture ingress sensor.

Other aspects and advantages of the invention will become apparent from the following detailed description taken in conjunction with the accompanying drawings which illustrate, by way of example, the principles of the described embodiments.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Common issues still prevalent in many electronic devices are corrosion and damage caused by moisture ingress. Moisture can invade various portions of a computing device causing shorts that create conductive pathways to areas of the computing device not intended to receive certain amounts of current. Although many computing device housings are intended to be sealed, moisture can still find a way to enter computing device housings. In order to deal with this ingress, embodiments of a moisture ingress sensor (also referred to as an ingress sensor) are provided herein. The moisture ingress sensor uses a passive component for detecting moisture ingress. The passive component is electrically coupled to an active current source having a resistor, N-channel metal oxide semiconductor field effect transistor (MOSFET), an operational amplifier, two comparators, and an AND logic gate. This configuration for the moisture ingress sensor provides a low powered means for detecting moisture ingress while also producing accurate moisture ingress indication. Moreover, the moisture ingress sensor operates on a low frequency and low voltage duty cycle thereby utilizing less power from a battery of the computing device. The moisture ingress sensor can send one or more moisture indication signals to a computing device in which the moisture ingress sensor is incorporated. In this way, the computing device can react appropriately to the detection of moisture by shutting down a portion of the computing device and/or isolating a portion of the computing device. Moreover, the ingress sensor can be incorporated into printed circuit boards, flexible circuits, and integrated circuits allowing the ingress sensors to be placed near potential ingress locations, while taking up very little space. Multiple ingress sensors can be incorporated into a single computing device for detecting moisture ingress at numerous areas of the computing device. The ingress sensor can also be used for tracking data associated with moisture ingress events, and/or sending notifications to a user of the computing device. The computing device can also stop function of the ingress sensor by switching open a bias switch in order to mitigate corrosion and dendrite growth.

These and other embodiments are discussed below with reference to FIGS. 1A-11; however, those skilled in the art will readily appreciate that the detailed description given herein with respect to these figures is for explanatory purposes only and should not be construed as limiting.

Figure 1A:
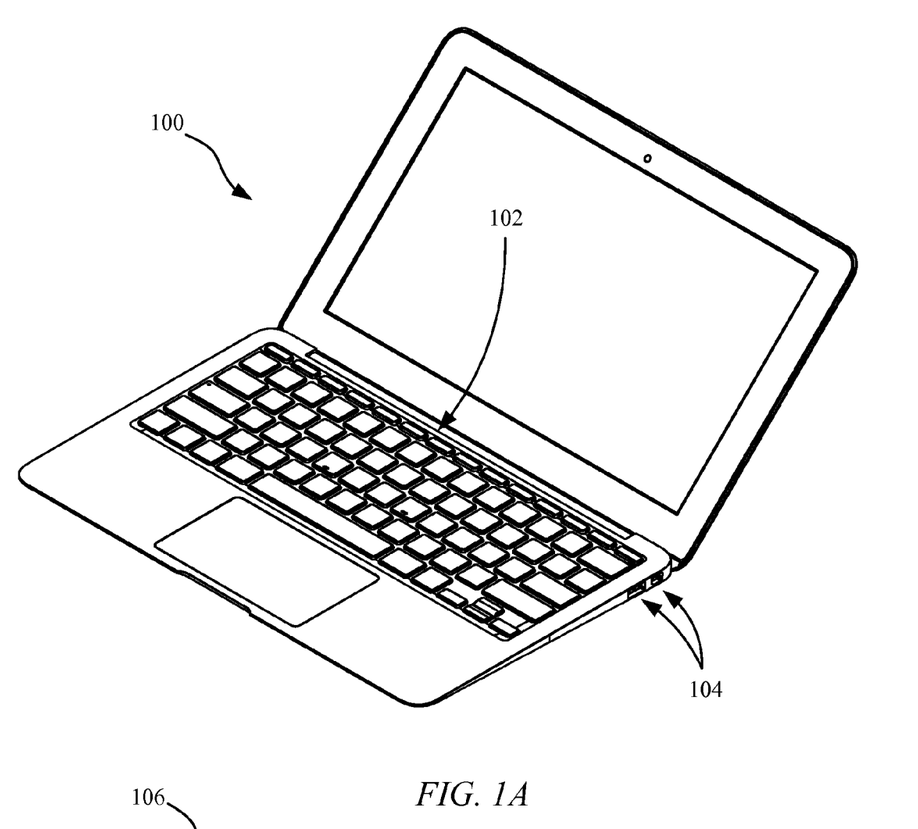
FIG. 1A-1B illustrate perspective views of points of potential moisture ingress of various computing devices.
Figure 1B:
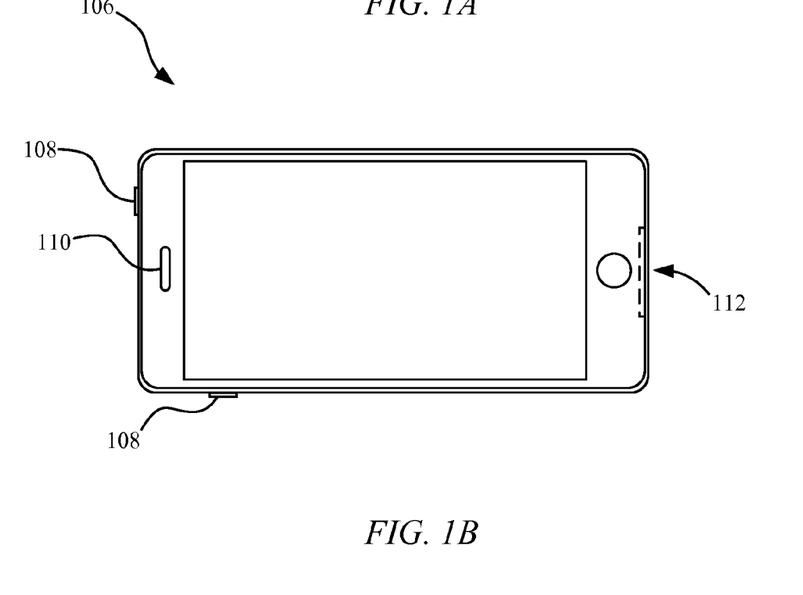

FIG. 1A-1B illustrate perspective views of potential points of moisture ingress for various computing devices. Specifically, FIG. 1A-1B show certain points susceptible to water ingress that can potentially damage or destroy the functionality of a computing device. In FIG. 1A, a laptop computing device 100 is illustrated as having multiple cavities that can provide entry for moisture. These entry ways can include keys of a keyboard 102 and external device ports 104. FIG. 1B illustrates a portable computing device 106, such as a cell phone, which can also have multiple entry ways for moisture to enter the device. For example, the portable computing device 106 can include a speaker aperture 110, various buttons 108, and a charging port 112. These cavities and entry ways of FIGS. 1A-1B, although useful for many functions of the devices, can be the reason for the degeneration of the device. Because of the nature of many liquids, a variety of internal components such as a main logic board can come into contact with moisture despite not being proximate to an entry of cavity of the device. The embodiments discussed herein are directed toward handling the entry of moisture into a computing device. In particular, the embodiments herein describe circuits for detecting and handling moisture that a computing device may come into contact with, and mitigating any damage that might be caused by the moisture.

Figure 2A:
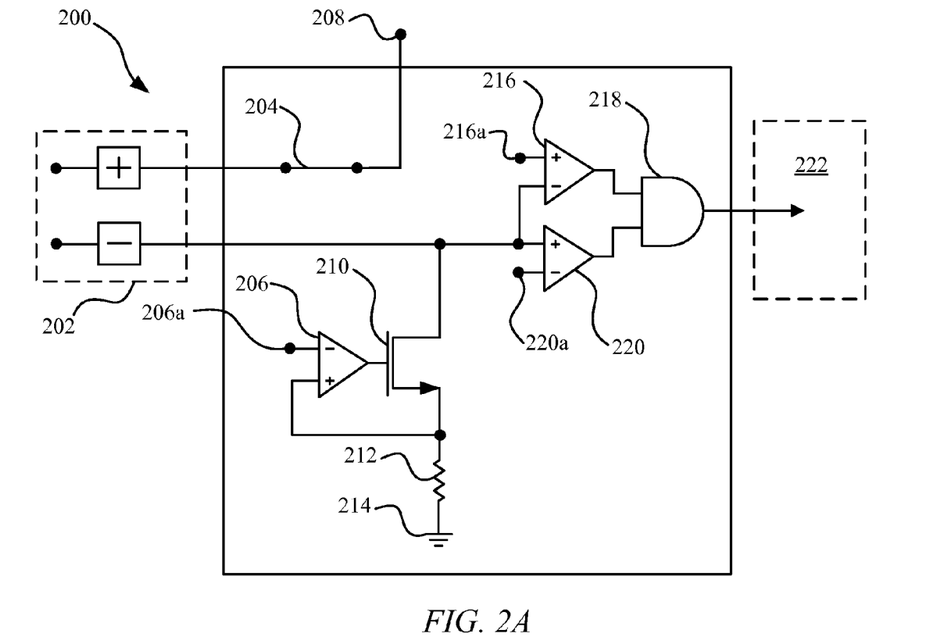
FIG. 2A-2B illustrate diagrams of an ingress sensor circuit according to some of the embodiments described herein.
Figure 2B:
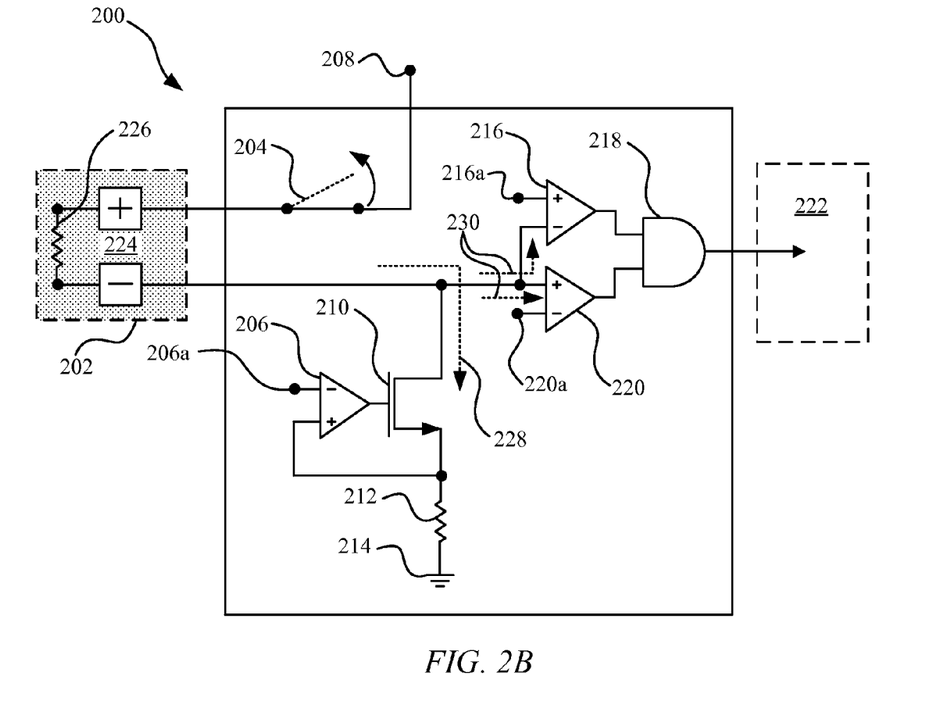

FIG. 2A-2B illustrate diagrams of an ingress sensor circuit according to some of the embodiments described herein. In particular, FIG. 2A-2B illustrate the arrangement of the circuit components for the ingress sensor described herein. It should be noted that the term "sensor" can include one or more components when referring to the various embodiments described herein. For example, the ingress sensor 200 of FIGS. 2A-2B includes multiple components in order to indicate a presence of moisture in or near a computing device. In particular, ingress sensor 200 includes a moisture interface 202 that is configured to interface with any moisture that enters the computing device. The computing device can be one of the computing devices illustrated in FIGS. 1A-1B or any other computing device that can incorporate protection from moisture such as a media player, server, desktop computer, etc. The computing device can receive data related to liquid ingress from the ingress sensor through a logic component 218 of the ingress sensor. In some embodiments, the logic component 218 is an AND gate that can indicate a "1" or a "0" depending on the detection or lack of detection of moisture, respectively. Moreover, in some embodiments the logic component 218 can be an "OR" gate or any other suitable logic gate, alone or in combination with other logic gates in order to provide an indicator for the detection of moisture.

In order to accurately distinguish moisture detection signals originating from the moisture interface 202, the ingress sensor 200 can further include a first comparator 216 and a second comparator 220 for providing a tolerance threshold for the moisture detection signals. In some embodiments, the first comparator 216 can be configured to compare a variety of moisture detection signals to a high tolerance voltage 216*a*. The high tolerance voltage 216*a* can be set at any suitable voltage for a particular design or comparator. In some embodiments, the high tolerance voltage 216*a* is set at approximately 0.505 volts. Similarly, the second comparator 220 can be configured to compare a variety of moisture sensor detection signals to a low tolerance voltage 220*a*. The low tolerance voltage 220*a* can be set to any suitable voltage for a particular design or comparator. In some embodiments, the low tolerance voltage 220*a* is set at approximately 0.495 volts. Additionally, in some embodiments the difference between the high tolerance voltage 216*a* and the low tolerance voltage 220*a* can be set at 0.010 volts, or any suitable voltage that is appropriate for a particular circuit. For example, some ingress sensors 200 may require a smaller or larger tolerance depending on the tuning of the circuit and the purpose of the sensor.

The sensing portion of the ingress sensor 200 is provided in part by the moisture interface 202. The moisture interface 202 can be comprised of a variety of materials such as metal, plastic, glass, liquids, gases, etc., or air gap, in order to provide measurable signal when the moisture interface 202 contacts a liquid, gas, or any other molecule that could be harmful to the computing device in which the ingress sensor 200 is incorporated. In some embodiments, the moisture interface is configured such that when moisture 224 contacts the moisture interface 202, the moisture interface 202 converts from a high or low resistance (as shown in FIG. 2A) into a low or high resistance circuit having a moisture resistance 226 (as shown in FIG. 2B), respectively. The value of moisture resistance 226 depends on the configuration of the ingress sensor 200 and the type of moisture that the moisture interface 202 has come into contact with. Additionally, the value of measurable resistance can determine the variance of the moisture detection signal that is sent to the logic component 218, and other components 222 of the computing device.

In order to provide an accurate moisture detection signal to the logic component 218, the ingress sensor 200 includes a combination of electrical components for comparing electrical signals. Specifically, the ingress sensor 200 can include an N-channel metal oxide semiconductor field effect transistor (MOSFET) 210 that can be connected to an operational amplifier 206, bias resistor 212, and the moisture interface 202. The N-channel MOSFET 210 can be biased to a particular voltage determined by the reference voltage 206a of the operational amplifier 206. In this way, the logic component 218 can receive the reference voltage 206a and a reference signal 230 when the N-channel MOSFET 210 is activated by an activating current 228. For example, when the moisture interface 202 is not contacting moisture, the moisture interface 202 remains as a highly resistive circuit or open circuit thereby preventing any current from moving through the N-channel MOSFET 210, as shown in FIG. 2B. Alternatively, when moisture interface 202 comes into contact with moisture, the moisture interface 202 allows the activating current 228 to travel between a bias voltage 208 and bias switch 204, and through the moisture interface 202, and the N-channel MOSFET 210. Depending on the tuning of the ingress sensor 200, the activating current 228 will cause a conductive pathway to be created at the N-channel MOSFET 210 allowing the reference voltage 206a to be applied across the logic component 218 and ground 214, and a reference signal 230 to be sent through the first comparator 216 and second comparator 220. The reference signal 230 can then be characterized by the logic component 218.

The ingress sensor 200 can be tuned in a variety of ways in order to be activated by certain liquids or molecules. For example, the moisture interface 202 can be configured for specific liquids, including, but not limited to, water. Water has a resistivity of approximately 18 mega-ohm centimeters (MΩ cm). If the contacts of the moisture interface 202 are spaced apart by 0.5 millimeters (mm) and the moisture interface has a total surface area of 1 cm², then the measured resistance at the contacts of the moisture interface 202 will be 0.9 MΩ based on the following formula:

$$R = \frac{\rho L}{A} = 18 \text{ M}\Omega \cdot \text{cm} \times \frac{0.05 \text{ cm}}{1 \text{ cm}^2} = 0.9 \text{ M}\Omega \qquad (1)$$

In some embodiments, based on this calculated resistance value, the remaining portions of the ingress sensor 202 can be configured to not only send a signal indicating that moisture is present, but also design an ingress sensor 202 that consumes very little power. For example, by using a reference voltage 206a of 0.5 volts, the bias resistor 212 can be modified in order to establish an activating current 228 that is as low as possible while still being high enough to induce a conductive pathway in the N-channel MOSFET 210. In some embodiments, the bias resistor 212 has a value of approximately 500 kΩ. Additionally, in some embodiments, the total sensor power can be approximately between 18-20 microwatts.

The bias switch 204 is configured to open and close after the logic component 218 has indicated that moisture 224 is present at the moisture interface 202. In this way, the bias switch 204 acts as a safety mechanism to prevent further damage caused by the moisture 224. Such damage can include corrosion or dendrite growth, which can be exacerbated by the presence of charge such as the bias voltage 208. Other portions of the computing device, in which the ingress sensor 200 can be incorporated, can also be shut off or isolated as a result of a detection of moisture 224. For example, if the moisture interface 202 is near a camera flash of a computing device and the moisture interface 202 detects moisture 224, the logic component can send an indication to the computing device that moisture 224 is present near the camera flash. As a result, the computing device can execute an application or set of instructions that shuts down the camera flash and prevents further use of the camera flash. The computing device can also shut down components and/or devices neighboring the camera flash, in order to isolate the camera flash. The computing device can record the received indicators from the ingress sensor 200 and keep a record of where, when, and what time the presence of moisture 224 occurs.

Figure 3:
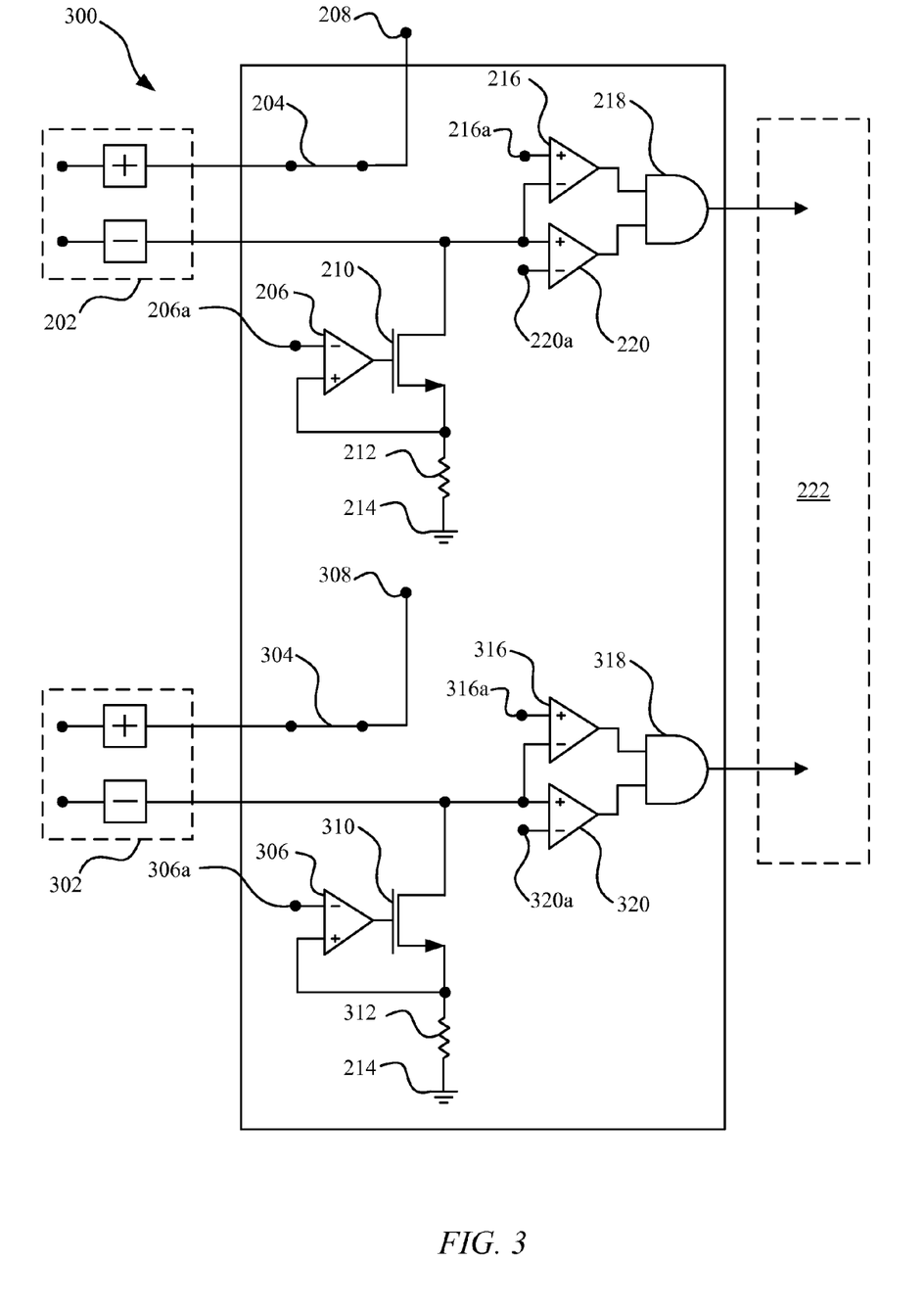
FIG. 3 illustrates an ingress sensor circuit diagram having multiple moisture interfaces.

FIG. 3 illustrates an ingress sensor 300 circuit diagram having multiple moisture interfaces. In particular, the ingress sensor 300 is configured to have the moisture interface 202 and an additional moisture interface 302 located at different portions (e.g., on and around a main logic board) of a computing device. In this way, multiple parts of the computing device can be monitored and protected from moisture. It should be noted that FIG. 3 includes all of the elements of FIGS. 2A and 2B, and an additional set of elements to accommodate the additional moisture sensor 302. For example, as compared to FIGS. 2A-2B, ingress sensor 300 also includes a bias voltage 308 and bias switch 304 that can supply a same or a different voltage, and be triggered in a same or a different way than the ingress sensor 200. Additionally, the tuning of the ingress sensor 300 can be modified such that the MOSFET 310, operational amplifier 306, reference voltage 306a, and/or bias resistor 312 detect a type of moisture that is different than the moisture detected by the moisture interface 202. Moreover, the voltage tolerance for detecting moisture can be modified such that a high tolerance voltage 316a and a low tolerance voltage 320a are different than the tolerances of ingress sensor 200. In this way, a first comparator 316 and second comparator 320 can be set to be more or less strict when detecting a voltage resulting from the detecting of moisture. This modification to tolerances and thresholds can cause the logic component 318 to indicate moisture more or less often, or at the same time, as the logic component 218.

The ingress sensor 300 of FIG. 3 can be configured to provide the computing device with indicators for types of liquids detected at the moisture interface 202 and 302. In some embodiments, the components connected to moisture interface 202 can be tuned differently than the components connected to moisture interface 302 such that moisture interface 202 indicates the presence of moisture differently than moisture interface 302 detects moisture. For example, moisture interface 202 can be configured to detect oils while moisture interface 302 can be configured to detect water. Upon the detection of either oil or water, logic component 218 or logic component 318, respectively, will provide an indicator to the other components 222 of the computing device. The types of moisture detected can be classified, ranked, and stored within the computing device for later use, or acted on immediately by the computing device. Additionally, in some embodiments, if the moisture interfaces 202 and 302 detect moisture at the same time, a more invasive operation could be performed by the computing device to protect the computing device. For example, in some embodiments, the battery of the computing device can be completely isolated from the computing device by a switching mechanism when the ingress sensor 200 and/or the ingress sensor 300 detect a certain type of liquid, detect a liquid a certain number of times, and/or detect a liquid for a certain period of time. Additionally, in some embodiments, the safety procedures of the computing device can be based on an integral or derivate operation of the incoming data from the ingress sensor 200 or 300.

Figure 4A:
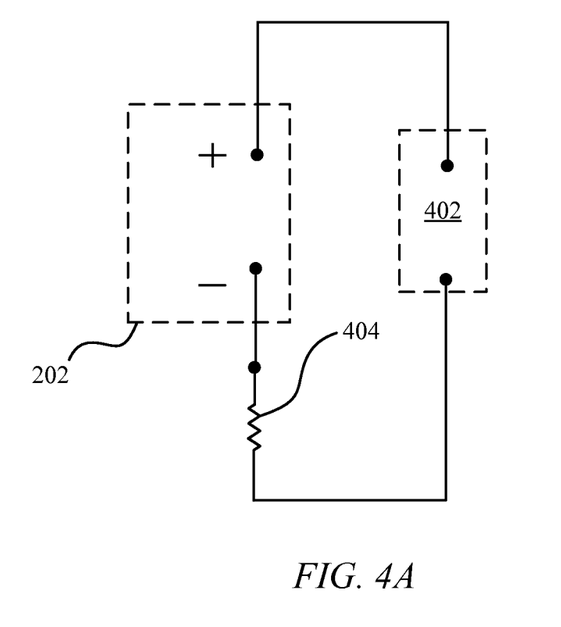
FIG. 4A-4B illustrate circuit diagrams of a portion of the ingress sensor according to some embodiments described herein.
Figure 4B:
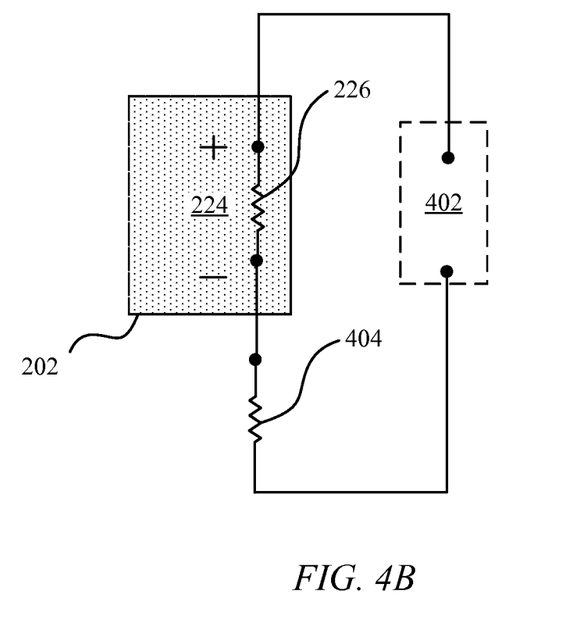

FIG. 4A-4B illustrate circuit diagrams of a portion of the ingress sensor according to some embodiments described herein. Specifically, FIG. 4A illustrates the moisture interface 202 incorporated into a representative version of the ingress sensor for purposes of explaining the tuning process of the ingress sensor according to some embodiments. The moisture interface 202 can be configured as an open circuit as provided in FIG. 4A such that an almost infinite resistance would be measured at an ohm meter 402, basically preventing any current from passing through moisture interface 202. In some embodiments, the moisture interface 202 can allow for some leakage of current over the moisture interface 202 and a base resistance 404 to be measured. When tuning the ingress sensor with respect to some embodiment described herein, the base resistance 404 should be taken into account in order to provide a more accurate indicator of moisture ingress to a computing device. For example, as illustrated in FIG. 4A, when moisture 224 is received by the moisture interface 202, a new resistance value will be measured at the ohm meter 402. The new resistance value will be a total of the base resistance value 404 and the moisture resistance 226. By taking into account the new resistance value, a designer can modify the base resistance and input voltage of the circuit in order to lower the total power for the ingress sensor while also providing an accurate indicator of moisture ingress.

Figure 5A:
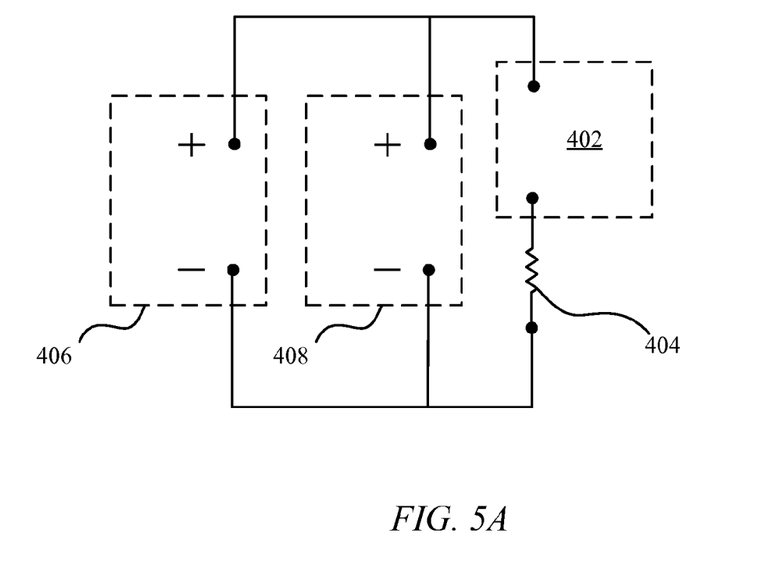
FIG. 5A-5B illustrate circuit diagrams of a portion of the ingress sensor according to some embodiments described herein.
Figure 5B:
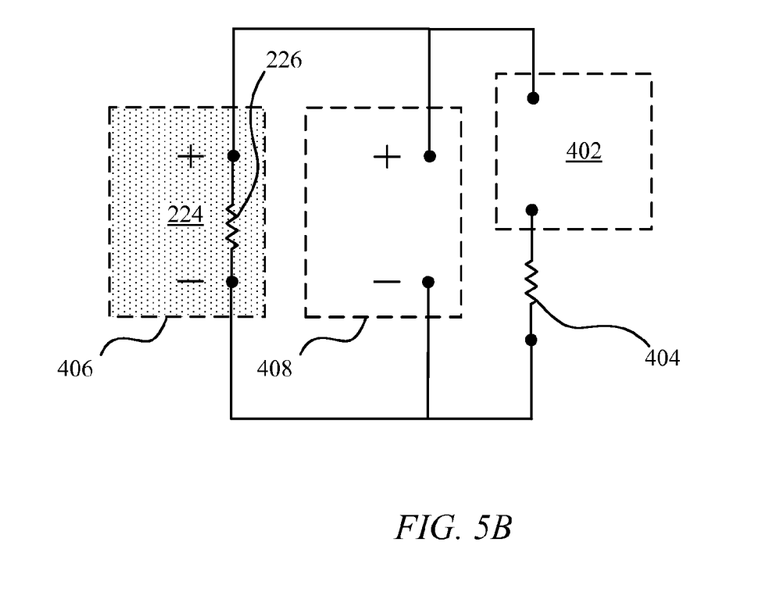

FIG. 5A-5B illustrate circuit diagrams of a portion of the ingress sensor according to some embodiments described herein. Specifically, FIG. 5A illustrates an embodiment of the ingress sensor having multiple moisture interfaces. A first moisture interface 406 is configured in parallel to a second moisture interface 408 in order to provide multiple areas of a computing device with moisture ingress detection. The circuit of FIG. 5A can be tuned in a similar manner as discussed with FIGS. 4A-4B. For example, the base resistance 404 would be measurable from an ohm meter 402 as either an almost infinite value in the case of both the first moisture interface 406 and the second moisture interface 408 being open circuits. In other embodiments, the first moisture interface 406 and the second moisture interface can allow for some current leakage in order to provide the ohm meter 402 with a finite base resistance 404. The first moisture interface 406 and the second moisture interface 408 can be made from the same materials, or different materials listed herein. As shown in FIG. 5B, when moisture 224 contacts the moisture interface 406, the moisture resistance 226 can be measured and compared to the resistance measured at the ohm meter 402. The computing device incorporating the ingress sensor can be configured to respond in a variety of ways depending on whether one or more of moisture interfaces detect moisture ingress. For example, as shown in FIG. 5B, the measured resistance at ohm meter 402 will be the total of the moisture resistance 226 and the base resistance 404; however, if moisture was present at the second moisture interface 408, the total resistance measured at ohm meter 402 (e.g., a parallel combination of two moisture resistance values plus the base resistance 404) would be adjusted accordingly. In this way, the resistance, voltage input, and indicators provided at the ingress sensor can be modified to have a low operating power, accurate moisture indication for both the first moisture interface 406 and second moisture interface 408, and detect a variety of moisture ingress scenarios at multiple areas of a computing device.

Figure 6A:
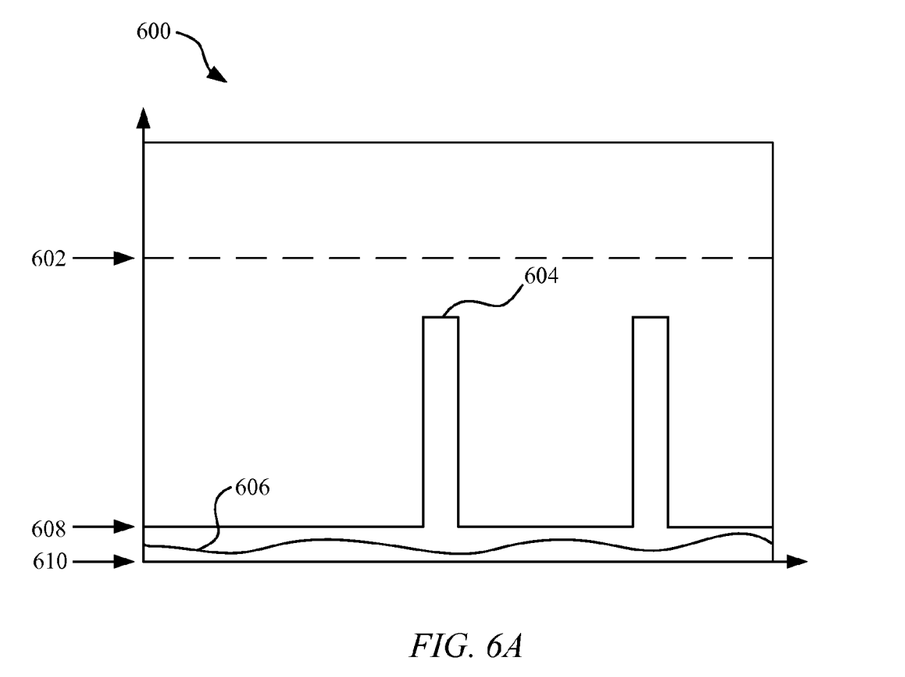
FIG. 6A-6B illustrate a graph of the signals transmitted during operation readings of the ingress sensor.
Figure 6B:
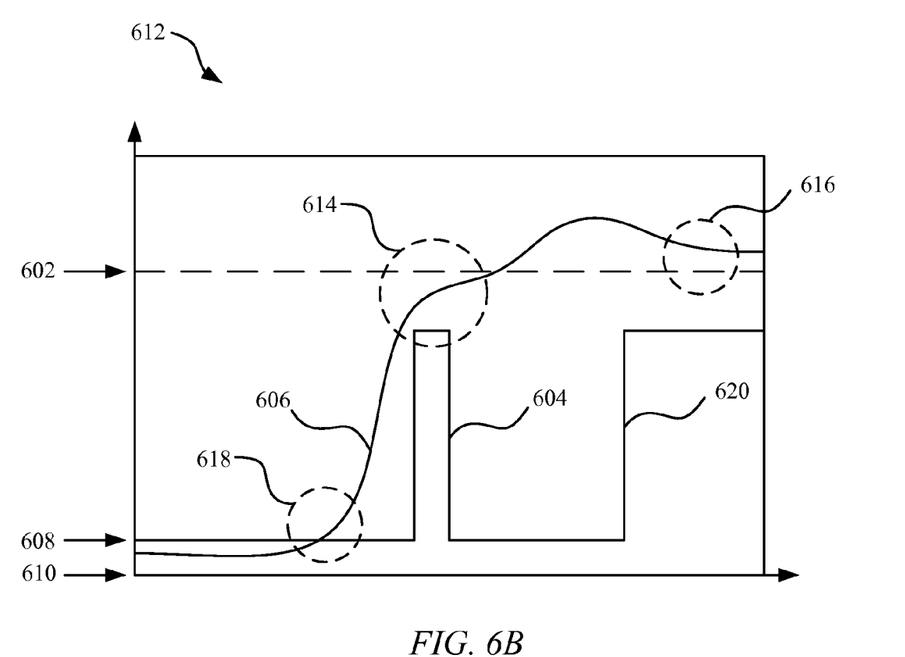

FIG. 6A-6B illustrate a graph of the signals transmitted during operation of the ingress sensor 200. Specifically, graph 600 illustrates a variety of signals transmitted during a non-moisture event of the ingress sensor 200 and graph 612 illustrates a variety of signals transmitted during a moisture event of the ingress sensor 200. In FIG. 6A, the duty cycle 604 is a pulse of voltage provided to the ingress sensor 200. The duty cycle 604 starts at zero volts 608 and pulses to a desired voltage value that can be adjusted, along with the period and frequency of the duty cycle 604. In some embodiments, the duty cycle includes a pulse having a length of one microsecond every second. In some embodiments, the pulse width can be between a 0.1-0.001 seconds. Additionally, the period between for a pulse can be about a second. These values can be increased or decreased for any suitable application. However, by keeping a low frequency and low pulse voltage, there is less opportunities for corrosion and dendrite growth near the ingress sensor 200.

FIG. 6A further illustrates the peak resistance 602 that can trigger the ingress sensor 200 to send a moisture indication to the computing device. As time 610 passes, the duty cycle 604 will pulse a voltage at the ingress sensor 200 in order to detect whether the resistance 606 at the moisture interface 202 has changed. In FIG. 6A, the resistance 606 stays below the peak resistance 602 during a non-moisture event. However, as shown in FIG. 6B, the duty cycle 604 will change at pulse 620 as a result of the ingress sensor 200 receiving moisture. At region 618, moisture ingress is beginning to occur as indicated by the resistance 606 increasing toward the peak resistance 602 over time. At region 614, the duty cycle 604 does not indicate moisture because the resistance 606 has not reached the peak resistance 602. However, at region 616, the resistance 606 is above the peak resistance 602 when the pulse 620 is initiated, and as a result the ingress sensor 200 will provide a moisture indication.

Figure 7A:
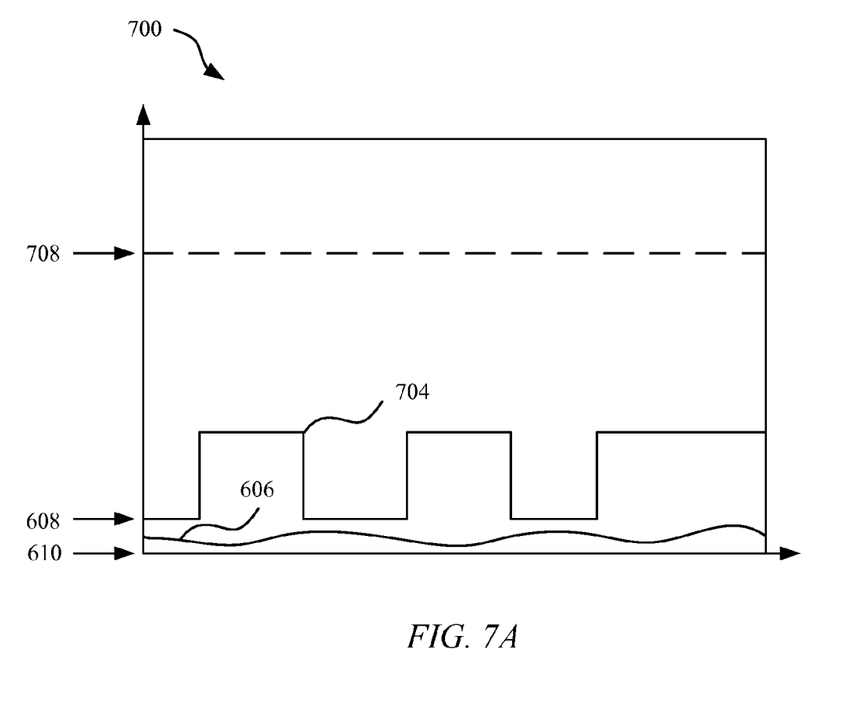
FIGS. 7A-7B illustrates a graph of the signals transmitted during operation of the ingress sensor according to some embodiments described herein.
Figure 7B:
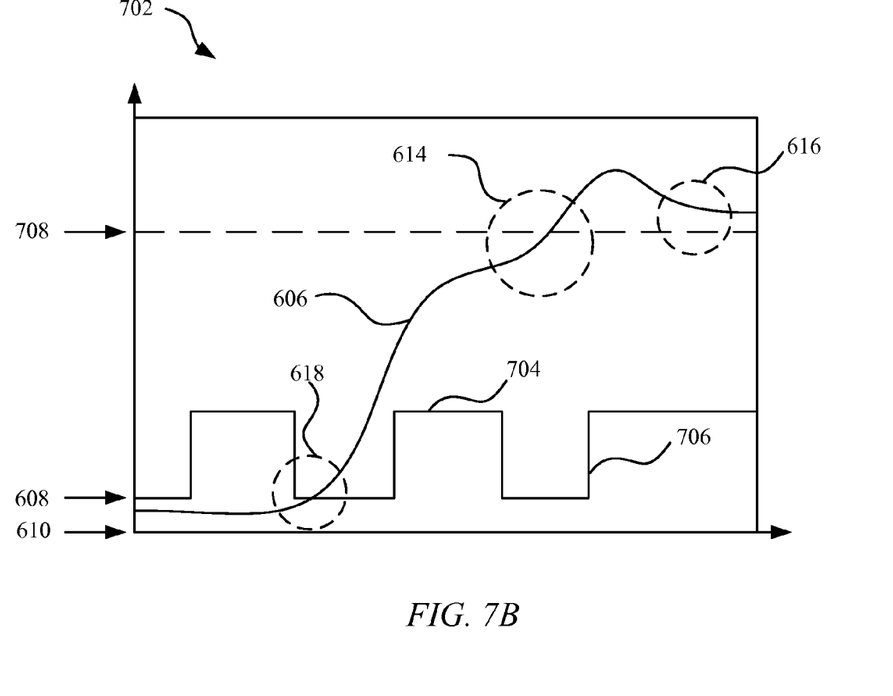

FIGS. 7A-7B illustrates a graph of the voltmeter readings of the ingress sensor 200 according to some embodiments described herein. In particular, FIGS. 7A-7B show an embodiment having a modified duty cycle 704. Although FIGS. 7A-7B incorporate many of the same elements of FIGS. 6A-6B, the modified duty cycle 704 is illustrated to provide an example of how the voltage, period, and frequency, of the duty cycle 604 can be modified in order to provide a lower voltage operation for the ingress sensor 200. In this way, the pulse 706 of FIG. 7B would be triggered at a modified peak resistance 708 because of the change in voltage of the duty cycle 704. Other changes can also be made to the duty cycle including modifying the shape of the wave form from a square to another shape such as a triangle, sine, cosine, sawtooth, etc. Additionally, the wave form can oscillate from a negative voltage to a positive voltage, wherein the negative and positive voltages can be the same or different. Moreover, in some embodiments, the duty cycle can be adjusted dynamically depending on operation of the computing device. For example, the duty cycle can be modified to account for a low battery indicator from the computing device in order to save energy.

Figure 8:
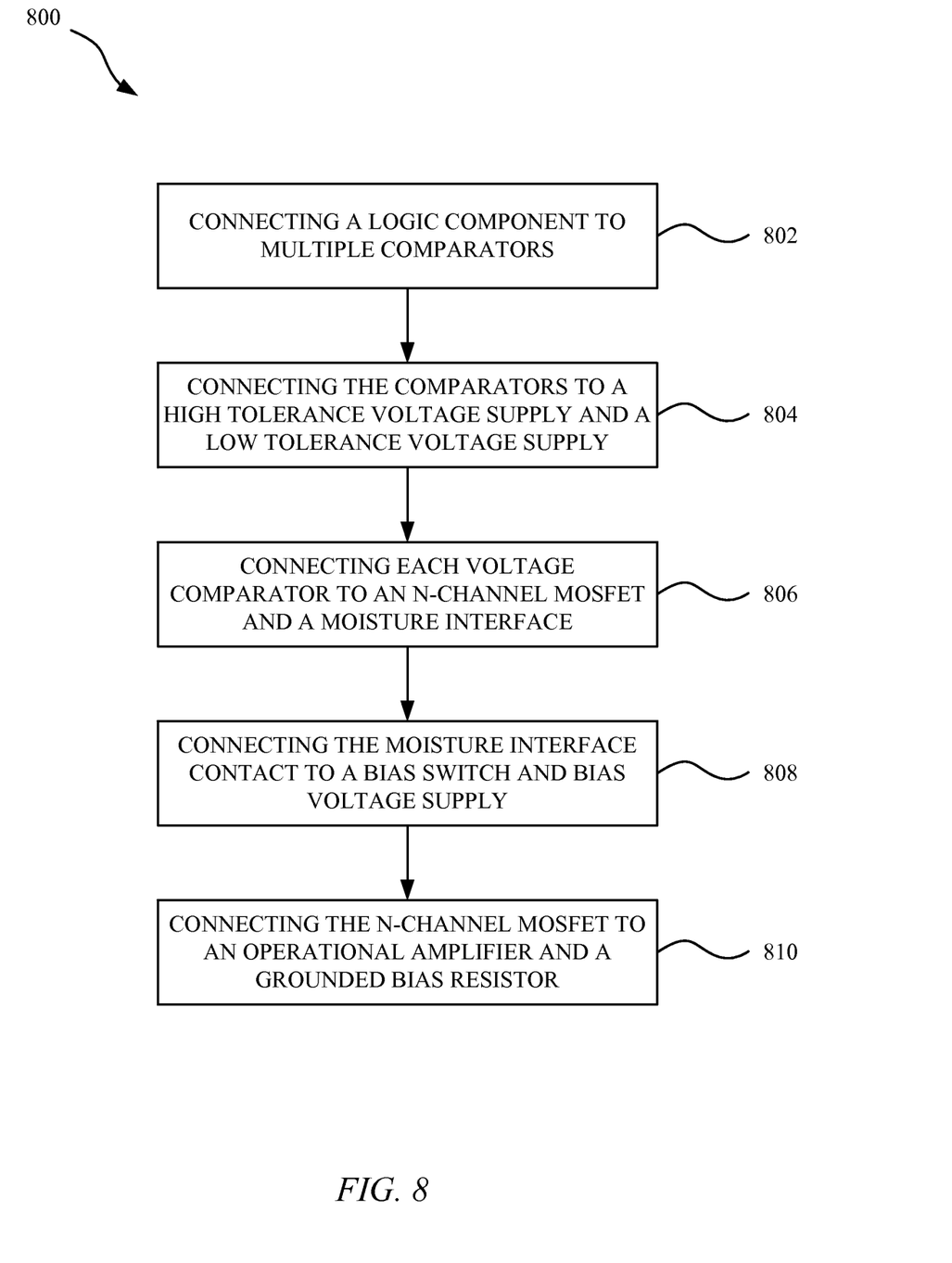
FIG. 8 illustrates a method for constructing the ingress sensor according to some of the embodiments described herein.

FIG. 8 illustrates a method 800 for constructing an ingress sensor according to some of the embodiments described herein. The method 800 can include a step 802 of connecting a logic component to multiple comparators. At step 804, the method 800 can include connecting the comparators to a high tolerance voltage supply and a low tolerance voltage supply. At step 806, the method 800 can include connecting each voltage comparator to an N-channel MOSFET and a moisture interface. Additionally, at step 808, the method 800 can include connecting the moisture interface contact to a bias switch and bias voltage supply. Furthermore, the method 800 can include a step 810 of connecting the n-channel MOSFET to an operational amplifier and a grounded bias resistor. The method 800 can be arranged in any suitable order or manner, and can be modified according to any of the embodiments described herein.

Figure 9:
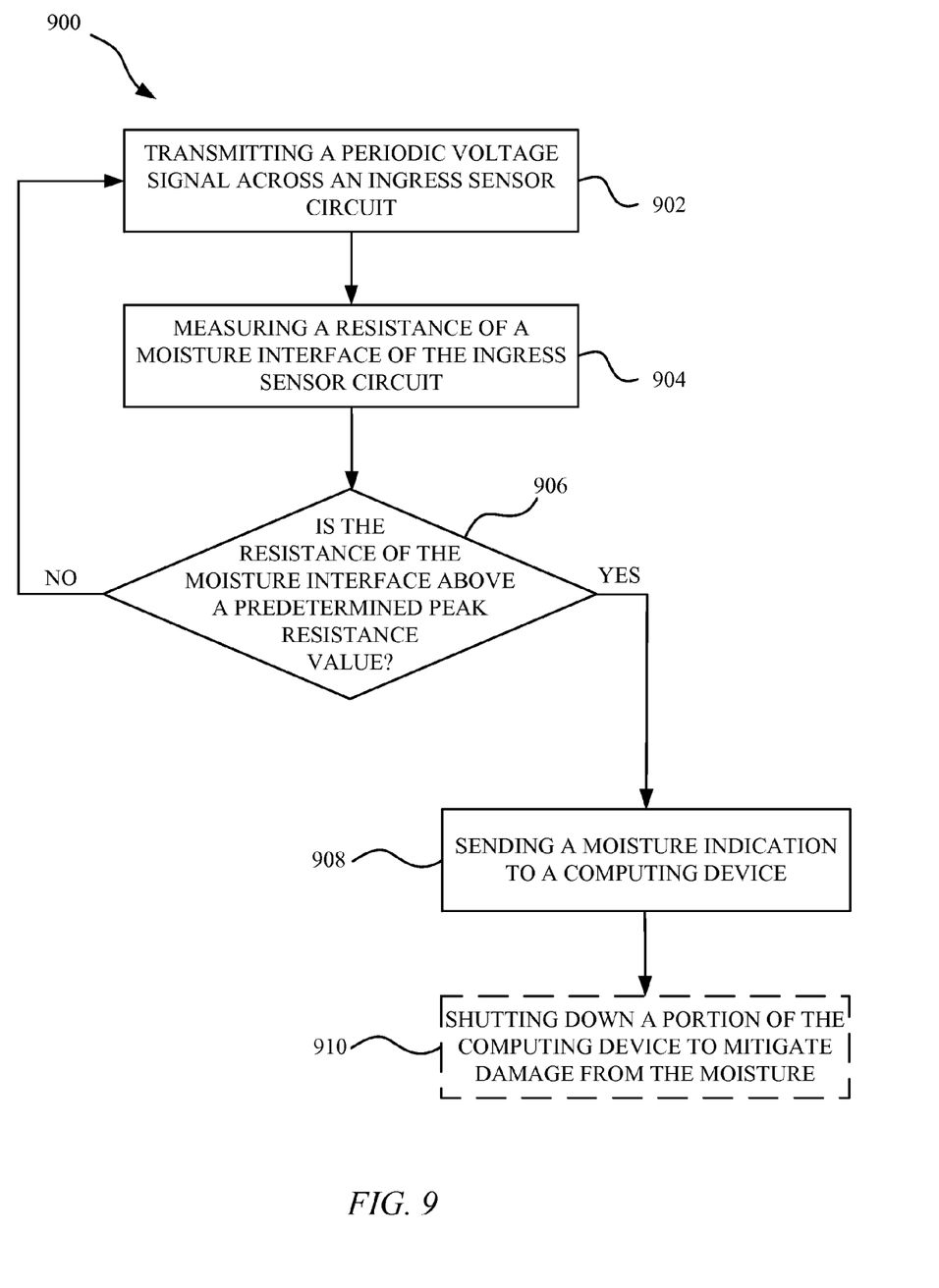
FIG. 9 illustrates a method for indicating a presence of moisture at the ingress sensor according to some embodiments.

FIG. 9 illustrates a method 900 for indicating a presence of moisture at the ingress sensor according to some embodiments. Specifically, FIG. 9 discloses a method 900 having a step 902 of transmitting a periodic voltage signal across an ingress sensor circuit. The voltage signal can be a duty cycle or any repetitive signal for energizing a portion of the ingress sensor. The method 900 further includes a step 904 of measuring a resistance of a moisture interface of the ingress sensor circuit. Upon measuring the resistance, a decision step 906 is provided for determining if the resistance of the moisture interface is above a predetermined peak resistance value. If the resistance of the moisture interface is below a predetermined peak resistance value, the method 900 returns to step 902 where the periodic voltage signal is sent across the ingress sensor. If the resistance of the moisture interface is above (or equal to, in some embodiments) a predetermined peak resistance value, the method 900 proceeds to step 908 wherein a moisture indication is sent to the computing device. The moisture indication can be a digital or analog signal based in part on the output of the ingress sensor. The method 900 further includes an optional step 910 of shutting down a portion of the computing device to mitigate damage from moisture. The method 900 can be arranged in any suitable order or manner, and can be modified according to any of the embodiments described herein.

Figure 10:
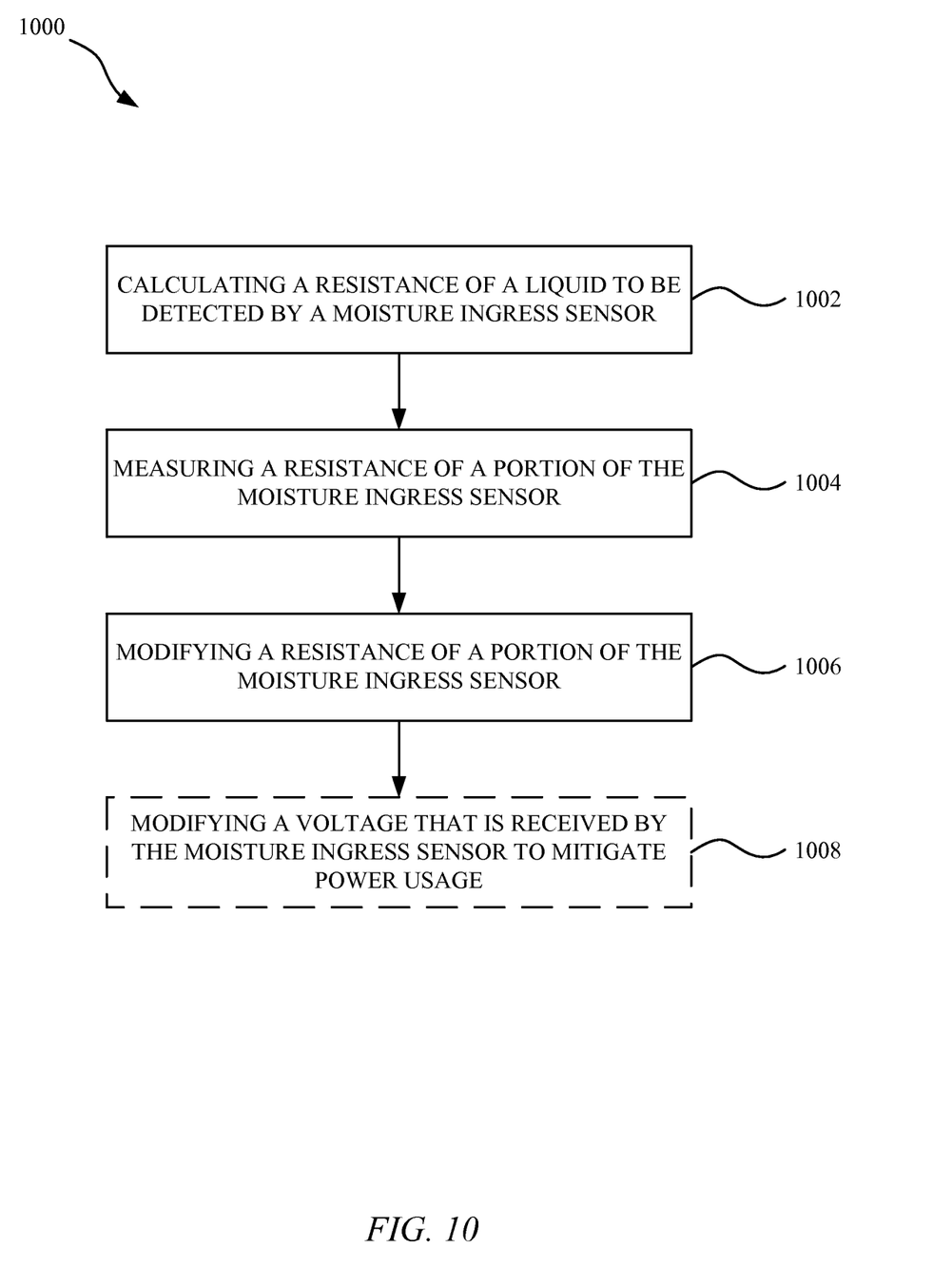
FIG. 10 illustrates a method of tuning the ingress sensor according to some embodiments described herein.

FIG. 10 illustrates a method 1000 of tuning the ingress sensor according to some embodiments described herein. The ingress sensor can be tuned in a variety of ways and for a multitude of applications. At step 1002 of method 1000, a resistance of a liquid to be detected by the moisture ingress sensor is calculated. This resistance value will be used in further steps to design the ingress sensor for the liquid to be detected. At step 1004, a resistance of a portion of the moisture ingress sensor is measured. The portion of the ingress sensor to be measured can be one or more components connecting a moisture interface to the ingress sensor, a component connecting the ingress sensor to ground, or any other suitable portion of the ingress sensor that provides a non-negligible resistance. At step 1006, the method 1000 includes modifying a resistance of a portion of the moisture ingress sensor to be approximately the resistance of the liquid, or a predetermined resistance value that indicates a presence of moisture, when the liquid contacts a moisture interface of the moisture ingress sensor. Step 1006 can be performed by increasing or decreasing the resistivity of a portion of the ingress sensor by adding and/or removing certain components of the ingress sensor. Furthermore, the method 1000 can include a step 1008 of modifying a voltage that is received by the moisture ingress sensor to mitigate power usage while providing an accurate indication of a presence of moisture. Step 1008 is an optional step a designer can take to reduce power consumption of the ingress sensor by considering the dependency of resistance on voltage and current. For example, should a designer prefer a very low current design, the resistance and voltage of the circuit can be modified accordingly, while also maintaining the accuracy of the ingress sensor when detecting moisture. The method 1000 can be arranged in any suitable order or manner, and can be modified according to any of the embodiments described herein.

Figure 11:
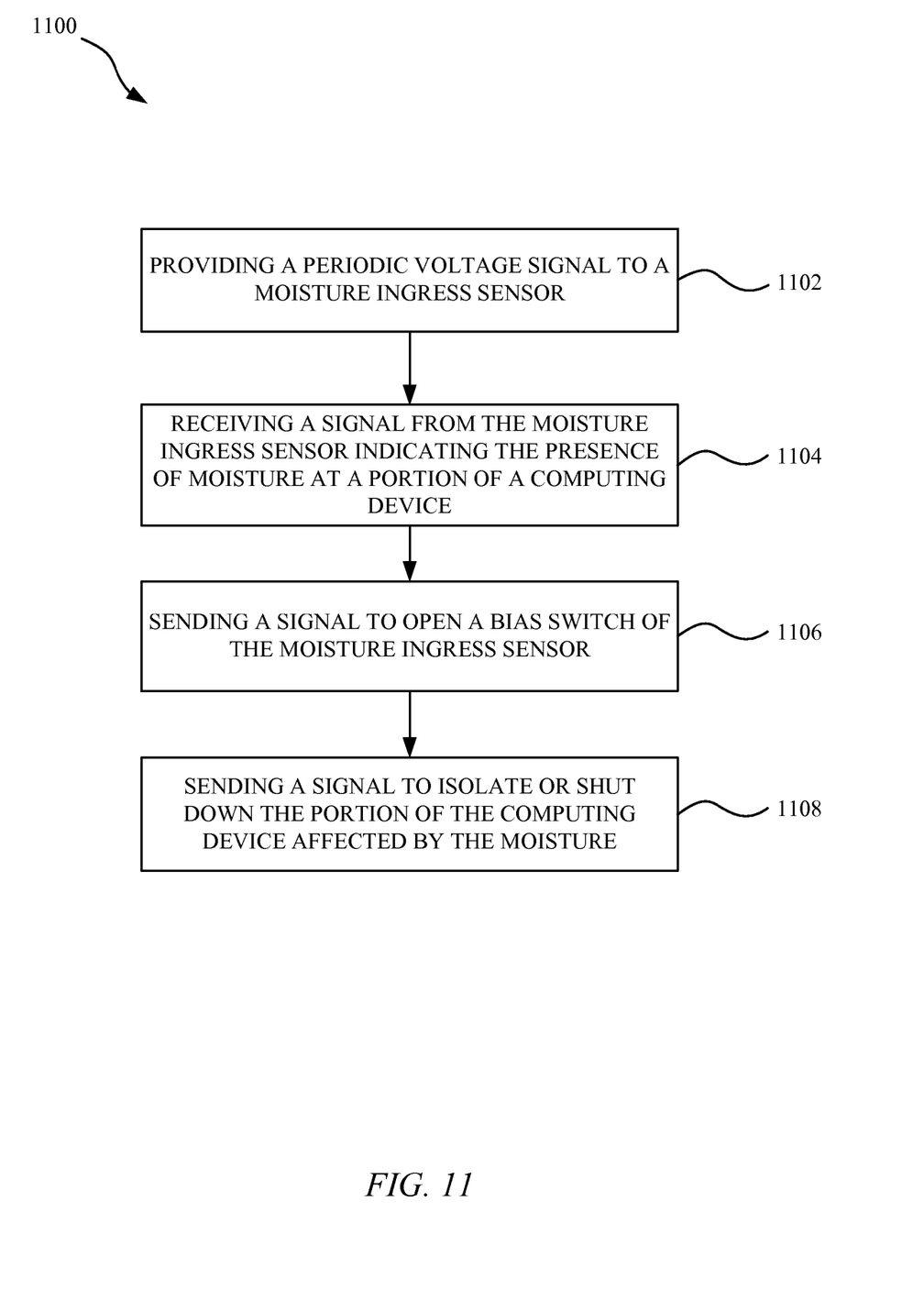
FIG. 11 illustrates a method of operating the ingress sensor of a computing device according to some embodiments described herein.

FIG. 11 illustrates a method 1100 of operating an ingress sensor of a computing device according to some embodiments described herein. The method 1100 includes a step 1102 of providing a periodic voltage signal to the moisture ingress sensor. At step 1104, the method 1100 includes receiving a signal from the moisture ingress sensor indicating the presence of moisture at a portion of the computing device. Moreover, the method 1100 can include a step of sending a signal to open a bias switch of the moisture ingress sensor. As discussed herein, opening the bias switch can be a preventative measure to reduce corrosion and dendrite growth at the point of moisture ingress. The method 1100 can further include sending a signal to isolate or shut down the portion of the computing device affected by the moisture. The method 1100 can be arranged in any suitable order or manner, and can be modified according to any of the embodiments described herein. For example, the computing device can send a signal to shutdown multiple portions of the computing device and keep a record in memory of the dates, times, types, severity, etc., of moisture ingress events.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A moisture sensor capable of detecting multiple moisture events, comprising:
a moisture interface element capable of providing an electrical parameter value associated with a moisture detection event, wherein a first moisture event comprises: the moisture interface element providing a first electrical parameter value having a first peak value that is less than a threshold value such that the moisture interface element is prevented from issuing an activation signal, and wherein, a second moisture event subsequent to the first moisture event comprises: the moisture interface element remaining operable to provide a second electrical parameter value having a second peak value that includes at least the first peak value such that when the second peak value is greater than the threshold value, the moisture interface element provides the activation signal;
a logic circuitry connected to the moisture interface element; and
a signal processing portion connected to the logic circuitry and the moisture interface element, wherein the signal processing portion is arranged to (i) receive the activation signal, and (ii) send a corresponding reference signal to the logic circuitry such that the logic circuitry uses the corresponding reference signal to provide a moisture indication signal that corresponds to the first or the second moisture event.

2. The moisture sensor of claim 1, wherein the moisture interface element is a passive component comprising a first node and a second node coupled to a bias voltage.

3. The moisture sensor of claim 1, further comprising:
a bias switch connected to the moisture interface element, wherein the bias switch is configured to allow the activation signal to pass through.

4. The moisture sensor of claim 3, wherein the bias switch opens in response to receiving the activation signal.

5. The moisture sensor of claim 1, wherein an electrical resistance of the moisture interface element is increased upon the detection of any of the first or second moisture events.

6. The moisture sensor of claim 1, wherein the logic circuitry comprises:
at least two comparators connected to the moisture interface element, and an AND gate connected to the at least two comparators, wherein the at least two comparators define a tolerance that determines when the AND gate will cause the logic circuitry to output the moisture indication signal.

7. The moisture sensor of claim 1, wherein the signal processing portion includes an insulated gate device.

8. The moisture sensor of claim 7, wherein the signal processing portion includes an operational amplifier, and the insulated gate device is biased to a reference voltage of the operational amplifier.

9. The moisture sensor of claim 1, wherein the threshold value is a peak resistance.

10. A moisture ingress sensor for minimizing damage to an electronic component of a device, comprising:
a moisture interface element having an electrical resistance that is adjusted upon exposure of the moisture interface element to a first moisture event such that: (i) when a result of a detection of the first moisture event exceeds a threshold, then issuing a first activation signal, otherwise (ii) when the result of the detection of the first moisture event is less than the threshold: adjusting the electrical resistance upon the exposure of the moisture interface element to a second moisture event, and issuing a second activation signal upon determining that the second moisture event exceeds the threshold;
a bias switch that is configured to open in response to receiving any of the first or second activation signals from the moisture interface element;
a logical component coupled to the moisture interface element; and
a signal processing portion connected to the moisture interface element, wherein the signal processing portion is capable of (i) receiving any of the first or second activation signals, and (ii) sending a corresponding reference signal to the logical component, thereby causing the logical component to utilize the corresponding reference signal to provide a moisture indication signal.

11. The moisture ingress sensor of claim 10, wherein the moisture interface element is a passive element that decreases in electrical resistance when the first or second moisture events exceed the threshold.

12. The moisture ingress sensor of claim 10, further comprising:
at least two comparators, wherein the at least two comparators define a high tolerance and a low tolerance.

13. The moisture ingress sensor of claim 12, wherein the signal processing portion includes an insulated gate device.

14. The moisture ingress sensor of claim 13, wherein the signal processing portion includes an operational amplifier, and the insulated gate device is biased to a reference voltage of the operational amplifier.

15. A method for detecting multiple moisture events by a moisture ingress sensor of a computing device, the moisture ingress sensor including a moisture interface element capable of providing an electrical parameter value associated with a detection of a moisture event, the method comprising:
when the moisture interface element detects a first moisture event:
providing a first electrical parameter value having a first peak value that is less than a threshold value such that the moisture interface element is prevented from issuing an activation signal to a logic component of the moisture ingress sensor;
when the moisture interface element detects a second moisture event subsequent to the first moisture event, the second moisture event causes the moisture interface element to provide a second electrical parameter value having a second peak value that includes at least the first peak value:
providing the activation signal to the logic component when the second peak value satisfies the threshold value,
causing the logic component to send a moisture indication signal, and
sending a switch signal to a bias switch that opens the bias switch of the moisture ingress sensor.

16. The method of claim 15, further comprising:
preventing further operation of an electronic component of the computing device when the second peak value of the second moisture event satisfies the threshold value.

17. The method of claim 15, wherein the activation signal is transmitted to a metal oxide semiconductor field effect transistor (MOSFET) and a reference voltage is transmitted to the logic component when the second peak value of the second moisture event satisfies the threshold value.

18. The method of claim 17, further comprising:
causing comparators to allow a reference voltage to proceed to the logic component when the reference voltage is within a predetermined tolerance of the comparators.

19. The method of claim 15, wherein the threshold value corresponds to a predetermined peak resistance value.

20. The method of claim 15, wherein an electrical resistance of the moisture interface element is increased upon the detection of any of the first or second moisture events.

* * * * *